United States Patent
Hatanaka

(10) Patent No.: US 9,761,110 B2
(45) Date of Patent: Sep. 12, 2017

(54) ALARM DEVICE, EXTRACORPOREAL CIRCULATOR, AND ALARM DEVICE CONTROL METHOD

(71) Applicant: TERUMO KABUSHIKI KAISHA, Tokyo (JP)

(72) Inventor: Yoko Hatanaka, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/256,824

(22) Filed: Sep. 6, 2016

(65) Prior Publication Data

US 2016/0371954 A1 Dec. 22, 2016

Related U.S. Application Data

(63) Continuation of application No. PCT/JP2015/057691, filed on Mar. 16, 2015.

(30) Foreign Application Priority Data

Mar. 17, 2014 (JP) .................................. 2014-053950

(51) Int. Cl.
  *G08B 19/00* (2006.01)
  *G08B 21/18* (2006.01)
  (Continued)

(52) U.S. Cl.
  CPC ........... *G08B 21/18* (2013.01); *A61M 1/1698* (2013.01); *A61M 1/3666* (2013.01);
  (Continued)

(58) Field of Classification Search
  CPC ...... G08B 19/00; G08B 21/18; A61M 1/1698; A61B 5/002
  (Continued)

(56) References Cited

U.S. PATENT DOCUMENTS

| 2011/0043366 A1* | 2/2011 | Osone | A61B 5/002 340/573.1 |
| 2015/0220763 A1* | 8/2015 | Porzelt | G08C 17/00 340/10.1 |
| 2016/0095971 A1* | 4/2016 | Kopperschmidt | A61M 1/3639 604/4.01 |

FOREIGN PATENT DOCUMENTS

| JP | 05020574 | 1/1993 |
| JP | 2006325750 | 12/2006 |

(Continued)

*Primary Examiner* — Tai T Nguyen
(74) *Attorney, Agent, or Firm* — MacMillan, Sobanski & Todd, LLC

(57) ABSTRACT

An alarm device for a medical instrument includes a first alarm-signal sound output device which outputs a first alarm signal, an output determination unit which determines whether the first alarm-signal output device is outputting the first alarm signal during the specific alarm condition, and an alarm-signal-output stop unit 39 for manually clearing outputting of the alarm signal. The alarm device is configured so that when the output determination unit determines that the first alarm-signal output device has not output the alarm signal, a second alarm-signal output device outputs a second audible alarm signal distinctive from the first audible alarm signal. The alarm device is configured so that when the stop unit does not manually clear a selected alarm signal within a predetermined time after beginning output of the alarm signal, then an audible output characteristic of the alarm signal is changed.

5 Claims, 5 Drawing Sheets

(51) Int. Cl.
*A61M 1/16* (2006.01)
*A61M 1/36* (2006.01)
(52) U.S. Cl.
CPC ....... *A61M 1/3667* (2014.02); *A61M 2205/18* (2013.01); *A61M 2205/581* (2013.01)
(58) Field of Classification Search
USPC .............................. 340/521, 551, 10.1, 573.1
See application file for complete search history.

(56) References Cited

FOREIGN PATENT DOCUMENTS

| | | |
|---|---|---|
| JP | 2009077869 | 4/2009 |
| JP | 2011087678 | 5/2011 |
| JP | 2011234805 | 11/2011 |
| JP | 2012242880 | 12/2012 |
| WO | 2014034108 A1 | 3/2014 |

* cited by examiner

ALARM DEVICE, EXTRACORPOREAL CIRCULATOR, AND ALARM DEVICE CONTROL METHOD

CROSS REFERENCE TO RELATED APPLICATIONS

This application is a continuation of PCT Application No. PCT/JP2015/057691, filed Mar. 16, 2015, based on and claiming priority to Japanese application no. 2014-053950, filed Mar. 17, 2014, both of which are incorporated herein by reference in their entirety.

TECHNICAL FIELD

The present invention relates to an alarm device for notifying a person concerned of the occurrence of an abnormality, an extracorporeal circulator having the alarm device, and an alarm device control method.

BACKGROUND ART

Medical instruments, etc. conventionally used in medical sites each have an alarm device because the actions and the like of the instrument are involved in the life of each patient. For example, when it is necessary to supply blood to a patient during an operation, etc., a medical instrument such as an extracorporeal circulator that has an artificial heart-lung apparatus or the like for circulating the patient's blood extracorporeally, and such an extracorporeal circulator is also provided with an alarm device (see, for example, Japanese patent publication JP2006-325750). In a case of the extracorporeal circulator, which circulates the patient's blood extracorporeally, the extracorporeal circulator is configured so that the alarm device operates and outputs an alarm signal when, for example, an abnormality in a flow rate or the like of the circulating blood or an abnormality in pressure or the like has been detected.

SUMMARY OF THE INVENTION

Technical Problem

Even if the extracorporeal circulator has such an alarm device, there remains a problem that a failure, etc. of the alarm device might result in a case where the alarm does not get through to a person concerned. This problem might cause a serious result of, for example, the medical instrument, etc. and has, therefore, become ineffectual.

An object of the present invention, therefore, is to provide an alarm device, an extracorporeal circulator, and an alarm device control method capable of increasing the likelihood that a person concerned is notified of the fact that an alarm signal has been output.

Means for Solving the Problems

The abovementioned object is attained by an alarm device for a medical instrument including: a first alarm-signal sound output device selectably outputting a first audible alarm signal in response to a specific alarm condition; an output determination unit determining whether the first alarm-signal sound output device is outputting the first audible alarm signal during the specific alarm condition; a second audible alarm-signal sound output device selectably outputting a second audible alarm signal distinctive from the first audible alarm signal; and an alarm-signal-output stop unit for manually clearing output of the alarm signal, wherein the alarm device is configured so that when the output determination unit determines that the first alarm-signal output device is not outputting the first alarm signal during the specific alarm condition, then the second alarm-signal sound output device outputs the second alarm signal, and wherein the alarm device is configured so that when the stop unit does not manually clear a selected alarm signal within a first predetermined time after the alarm signal begins to be selected, then an audible output characteristic of the alarm signal is changed.

According to the configuration, the alarm device is configured so that when the output determination unit determines that the first alarm-signal output device such as a loudspeaker has not output the alarm signal, the second alarm-signal output device which is another alarm-signal output device such as a buzzer outputs an alarm signal. Owing to this, even when an alarm signal cannot be output due to a failure, etc. of the first alarm-signal output unit such as the loudspeaker, the second alarm-signal output device such as the buzzer outputs an alarm signal; therefore, it is possible to prevent the occurrence of a situation where no alarm signal is output. Furthermore, according to the configuration, the alarm device is configured so that when the stop unit is not used to manually clear the alarm signal within a predetermined time after output of the alarm signal from the first alarm-signal output device such as the loudspeaker or the second alarm-signal output device such as the buzzer, output of the alarm signal is changed by, for example, changing a volume of the loudspeaker to maximum (i.e., the alarm signal is made more conspicuous). It is, therefore, possible to increase the likelihood that a nurse, etc. who is a concerned person is notified of the occurrence of the alarm signal.

Preferably, the alarm device is configured to be communicable with a terminal device carried by a person to be notified of the alarm signal, and the alarm device may further include a sensing unit sensing presence of a concerned person (such as a nurse) capable of recognizing the output of the alarm signal. The alarm device is configured so that when a manual stop information (i.e., an alarm clearing command) is not input via the alarm-signal-output stop unit within a predetermined time after change of output of the alarm signal and the sensing unit does not sense the presence of the person, then information about a fact of occurrence of the alarm signal is transmitted to the terminal device.

According to the configuration, the alarm device includes the sensing unit, such as a motion sensor sensing presence of a person capable of recognizing the output of the alarm signal, and the alarm device is configured so that when the stop information (clearing command) is not input from the alarm-signal-output stop unit within a predetermined time after change of output of the alarm signal and the sensing unit does not sense the presence of the person, information about the fact of occurrence of the alarm signal is transmitted to the terminal device carried by the person to be notified such as the nurse, etc. to be notified of the alarm signal. Therefore, even when the nurse, etc. who is the person to be notified is not present around the alarm device, it is possible to ensure that the person to be notified is notified of the fact of the alarm signal.

Preferably, the alarm signal includes a specific alarm signal composed of a combination of specific frequencies or tones. The combination or sequence of specific frequencies or tones can be used to indicate the specific conditions that triggered an alarm.

According to the configuration, the alarm signal is the specific alarm signal composed of a combination of specific frequencies which are recognizable using conventional electronic devices and methods; therefore, the output determination unit can clearly determine whether or not the alarm signal has been output and it is possible to initiate an alternate means to signal the alarm to the concerned person.

Preferably, an extracorporeal circulator includes: an artificial heart-lung apparatus; and an extracorporeal circulation management device managing extracorporeal circulation of blood, wherein the extracorporeal circular includes the alarm device as described above. For example, the alarm device may comprise a first alarm-signal sound output device selectably outputting a first audible alarm signal in response to a specific alarm condition. An output determination unit determines whether the first alarm-signal sound output device is outputting the first audible alarm signal during the specific alarm condition. A second audible alarm-signal output device can selectably output a second audible alarm signal distinctive from the first audible alarm signal. An alarm-signal-output stop unit is provided for manually clearing output of the alarm signal. The alarm device is configured so that when the output determination unit determines that the first alarm-signal output device is not outputting the first alarm signal (after being triggered during the specific alarm condition), then the second alarm-signal output device outputs the second alarm signal. The alarm device is further configured so that when the stop unit does not manually clear a selected alarm signal within a first predetermined time after the alarm signal begins to be selected, then an audible output of the alarm signal is changed.

The abovementioned object is attained by an alarm device for a medical instrument including: an alarm-signal output device outputting an audible alarm signal in response to occurrence of an alarm condition; a communication controller for communicating with a remote terminal device carried by a person to be notified of the alarm signal; and a sensing unit sensing presence of a nearby person capable of recognizing that the alarm signal has been output. The alarm device is configured so that when the sensing unit does not sense the presence of the nearby person, then information about occurrence of the alarm condition is transmitted to the terminal device.

The abovementioned object is attained by a control method for an alarm device of a medical instrument including: a first alarm-signal output device selectably outputting a first audible alarm signal in response to a specific alarm condition; an output determination unit determining whether the first alarm-signal output device is selectably outputting the first alarm signal; and an alarm-signal-output stop unit for manually clearing an output of the alarm signal. The control method including: outputting, by a second alarm-signal sound output device a second audible alarm signal when the output determination unit determines that the first alarm-signal sound output device is not outputting the first alarm signal during the specific condition; and changing an audible output characteristic of the alarm signal when the stop unit does not manually clear a selected alarm signal within a predetermined time after output of the alarm signal begins to be selected.

Advantage of the Invention

As described above, the present invention can provide an alarm device, an extracorporeal circulator, and an alarm device control method capable of ensuring that a concerned person concerned is notified of the fact that an alarm signal has been output.

DETAILED DESCRIPTION OF PREFERRED EMBODIMENTS

A preferred embodiment of the present invention will be described hereinafter in detail with reference to the accompanying drawings, etc.

Various technically preferred limitations are imposed on the embodiment to be described below because the embodiment is a preferred specific example of the present invention; however, the scope of the present invention is not limited to these aspects unless the wording to the effect that the present invention is limited is given in the following disclosure.

Figure 1:
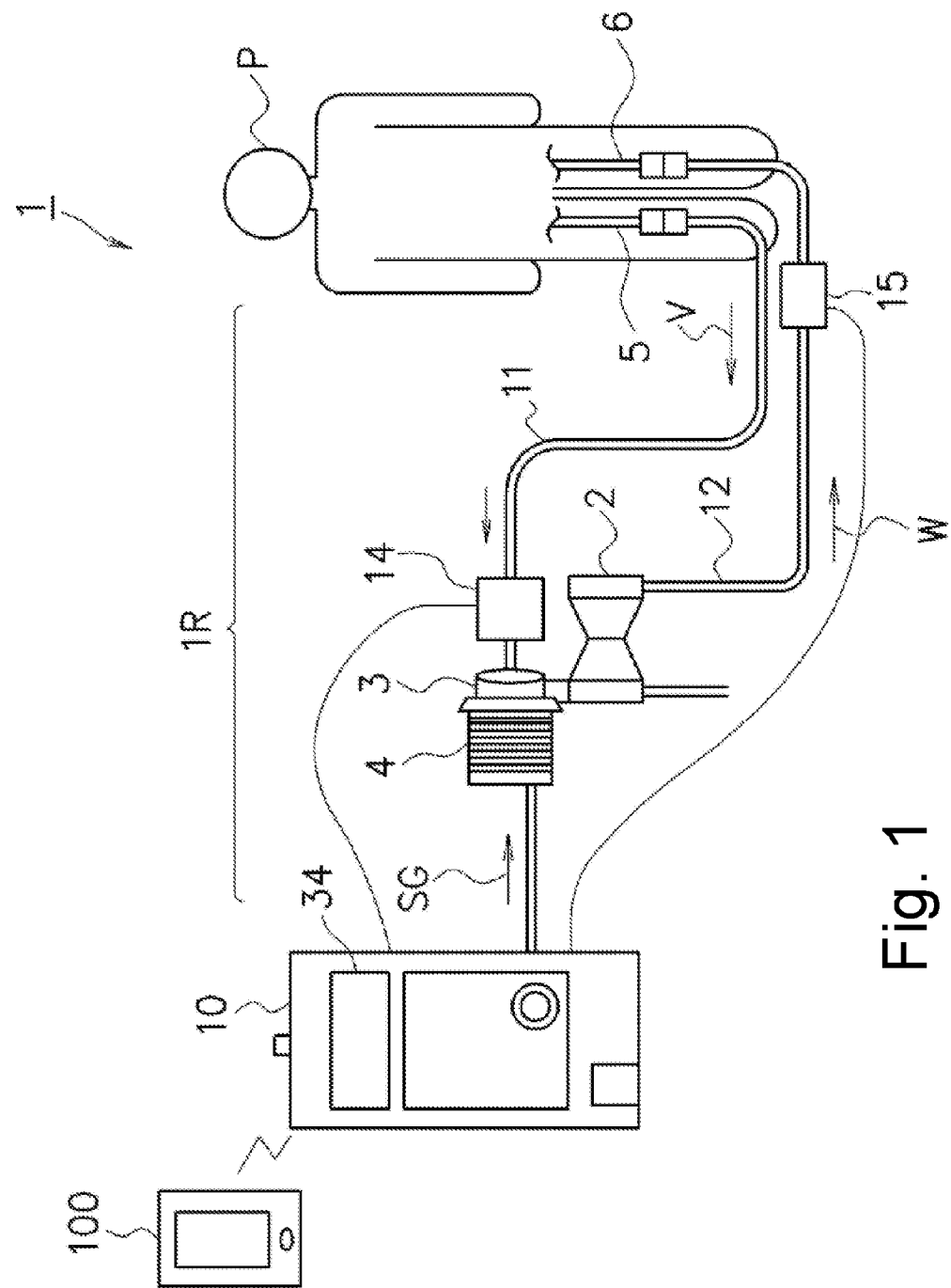
FIG. 1 is a schematic diagram illustrating main configurations of an extracorporeal circulator provided with an alarm device according to the present invention.

FIG. 1 is a schematic diagram illustrating main configurations of an extracorporeal circulator 1 provided with an alarm device according to the present invention. While the extracorporeal circulator 1 shown in FIG. 1 is a device for performing extracorporeal circulation of blood of a patient P, this "extracorporeal circulation" includes an "extracorporeal circulation action" and an "auxiliary circulation action". The "extracorporeal circulation action" is to perform a blood circulation action and a gas exchange action (oxygen addition and/or carbon dioxide removal) on this blood by means of this extracorporeal circulator 1 when the blood does not circulate in a heart of the patient (subject) P to which the extracorporeal circulator 1 is to be applied and natural circulation and gas exchange of the patient P has been stopped. Furthermore, the "auxiliary circulation action" is to assist in the blood circulation action by the extracorporeal circulator 1 when the blood circulates in the heart of the patient (subject) P to which the extracorporeal circulator 1 is to be applied and gas exchange can be implemented in a lung of the patient P. The extracorporeal circulator sometimes has a function to perform the gas exchange action on the blood depending on a type.

The extracorporeal circulator 1 according to the present embodiment as shown in FIG. 1 is used, for example, when a cardiac surgery is performed on the patient P or in a patient's room after the surgery. Specifically, a centrifugal pump 3 of the extracorporeal circulator 1 is actuated to perform "artificial lung extracorporeal blood circulation" for removing blood from a vein (main vein) of the patient P, implementing gas exchange within the blood by an artificial heart-lung apparatus which is, for example, an artificial lung 2 to oxygenate the blood, and then returning again this blood to an artery (main artery) of the patient P. Namely, the extracorporeal circulator 1 acts as a device which is an alternative to the heart and the lung.

Furthermore, the extracorporeal circulator 1 is configured as follows. Namely, as shown in FIG. 1, the extracorporeal circulator 1 has a "circulation circuit 1R" for circulating blood, and the circulation circuit 1R has the artificial heart-lung apparatus, which is, for example, the "artificial lung 2", the "centrifugal pump 3", a "drive motor 4", a "vein-side catheter (blood-removal-side catheter) 5", an "artery-side catheter (blood-transmission-side catheter) 6", and an extracorporeal circulation management device which is, for example, a controller 10. It is noted that the centrifugal pump 3 is also referred to as blood pump and a pump other than the centrifugal pump can be used.

The vein-side catheter (blood-removal-side catheter) 5 of FIG. 1 is inserted into a femoral vein and a tip end of the vein-side catheter 5 is indwelled in a right atrium. The artery-side catheter (blood-transmission-side catheter) 6 is inserted into a femoral artery. The vein-side catheter 5 is connected to the centrifugal pump 3 by using a blood removal tube 11. The blood removal tube (also referred to as "blood removal line") 11 denotes a duct for supplying blood. When the drive motor 4 drives the centrifugal pump 3 to operate in response to a command SG from the controller 10, the centrifugal pump 3 is configured to return the removed blood passed through the artificial lung 2 from the blood removal tube 11 to the patient P via a blood transmission tube 12 (also referred to as "solution transmission line").

The artificial lung 2 is disposed between the centrifugal pump 3 and the blood transmission tube 12. The artificial lung 2 performs a gas exchange action (oxygen addition and/or carbon dioxide removal) on this blood. The artificial lung 2 is, for example, a membrane-type artificial lung and a hollow fiber membrane-type artificial lung is particularly preferably used. The blood transmission tube 12 is a duct connecting the artificial lung 2 to the artery-side catheter 6. As each of the blood removal tube 11 and the blood transmission tube 12, a duct formed from synthetic resin such as vinyl chloride resin or silicone rubber exhibiting high clarity and flexibility can be used. The blood flows in a V direction within the blood removal tube 11, while the blood flows in a W direction within the blood transmission tube 12.

The extracorporeal circulator 11 has a "blood flow rate sensor 14" in the blood removal tube 11 thereof. This blood flow rate sensor 14 is configured to sense a value of a flow rate of the blood flowing from the patient P via the blood removal tube 11. Moreover, a "pressure sensor 15" is disposed on a patient P side in the blood transmission tube 12. This "pressure sensor 15" is configured to sense a pressure value of the blood within the blood transmission tube 12. Namely, the pressure sensor 15 is a sensor that measures a pressure of the blood passed through the duct in order to sense an abnormal pressure of the sensor.

A pressure abnormality of the blood often occurs due to the kink of the tube of the circulation duct 1R, the clogging of the artificial lung 2, the clogging of the centrifugal pump 3, etc., and this pressure abnormality possibly causes the occurrence of hemolysis (breakdown of red blood cells). Furthermore, as the pressure rises, the tube might be detached, possibly resulting in the leakage of the blood, etc. Considering the above, the extracorporeal circulator 1 has the pressure sensor 15 to measure the pressure of the blood in the duct, and the controller 10 is provided with the alarm device for issuing an "alert" or "alarm" under certain conditions when there occurs, for example, a pressure abnormality which is circulation abnormality information as described later.

The blood flow rate sensor 14 is a sensor which measures the flow rate value of the blood passed through the duct in order to sense an abnormality in the flow rate value. An abnormality in the flow rate value is caused by the kink of the tube of the circulation duct 1R, a reduction of revolving speeds of the drive motor 4 and the centrifugal pump 3, an increase of pressure loss, etc., and possibly causes poor circulation of the blood in the circulation duct 1R, which might produce hypoxia or the like to the patient.

Considering the above, the extracorporeal circulator 1 has the blood flow rate sensor 14 to measure the flow rate of the blood within the duct, and the controller 10 is provided with the alarm device for issuing an "alert" or an "alarm" under certain conditions when a flow rate abnormality occurs as described later. It is noted that, as the blood flow rate sensor 14, an ultrasound flow rate sensor or the like is used, for example.

The extracorporeal circulator 1 is configured so that when an abnormality in the flow rate or the like occurs to the blood in the duct and the blood is prevented from being supplied to the patient P while such an abnormal state continues, forceps are used on a controller 10-side of the pressure sensor 15 in the blood transmission tube 12 of FIG. 1 in order to be able to urgently close the blood transmission tube 12. It is noted that a display 34 for the display, etc. of various information is formed on the controller 10 as shown in FIG. 1.

Moreover, as shown in FIG. 1, the controller 10 of the extracorporeal circulator 1 is configured to be communicable with a remote terminal device, for example, a cellular telephone 100 that is carried by a person to be notified, for example, a nurse.

The controller 10, etc. of the extracorporeal circulator 1 shown in FIG. 1 have a computer, the computer has not only a CPU (Central Processing Unit) but also a RAM (Random Access Memory), a ROM (Read Only Memory), etc. which are not shown, and these elements are connected to one another via a bus.

Figure 2:
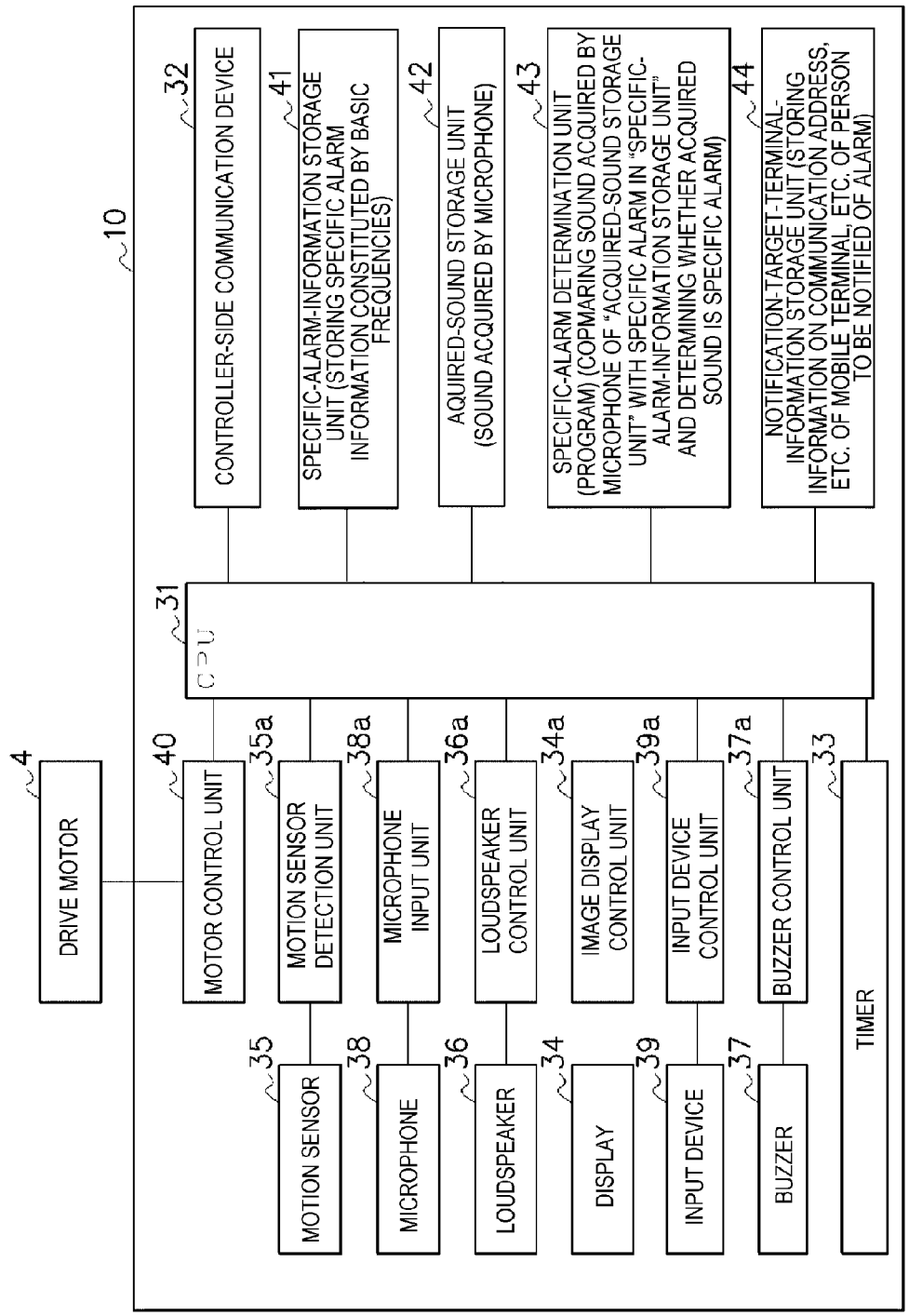
FIG. 2 is a schematic block diagram mainly illustrating configurations of an alarm device provided in a controller.

FIG. 2 is a schematic block diagram mainly illustrating configurations of the alarm device provided in the controller 10. As shown in FIG. 2, the alarm device has a CPU 31 that is a control unit of the controller 10 and the CPU 31 controls the following parts of the controller 10. That is, the controller 10 has a "controller-side communication device 32" by means of which the controller 10 communicates with the cellular telephone 100 (or other remote communication device that is monitored by a concerned person such as a nurse) shown in FIG. 1, a "timer 33" generating time information, the display 34, and an "image display control unit 34a" controlling the display 34, as shown in FIG. 2. The controller 10 also has a sensing unit which is, for example, a "motion sensor 35" and a "motion sensor detection unit 35a". This motion sensor 35 is a sensor that senses the presence of a nearby person, and may be comprised of, for example, a microwave sensor. Furthermore, the motion sensor detection unit 35a is configured to detect data of the motion sensor 35.

Moreover, the controller 10 has a first alarm-signal output device which is, for example, a "loudspeaker 36" outputting an alarm signal and a "loudspeaker control unit 36a". The alarm signal output from this loudspeaker 36 is a specific alarm signal composed of a combination of specific frequencies, e.g., a specific alarm tonal sequence (do, re, mi, fa, so, etc.) composed of basic frequency components equal to or lower than 1 kHz. Furthermore, the loudspeaker control unit 36a is configured to control this loudspeaker 36.

Moreover, the controller 10 has a second alarm-signal output device, for example, a "buzzer 37" outputting an alarm signal by a buzzer sound, and a "buzzer control unit 37a". This buzzer control unit 37a is configured to control this buzzer 37.

Furthermore, the controller 10 has a "microphone 38" that is responsive to the audible alarm from the loudspeaker 36, etc. and that converts the audible alarm into an electric signal, and a "microphone input unit 38a". This microphone input unit 38a is configured to, for example, receive the electric signal generated by the microphone 38.

Moreover, the controller 10 has an "input device 39" having a manually-activated stop switch, etc. that is an alarm-signal-output stop unit for stopping (i.e., canceling or clearing) output of the alarm signal, etc., and an "input device control unit 39a". This input device control unit 39a is configured to control the input device 39.

Moreover, the controller 10 has not only a "motor control unit 40" controlling the drive motor 4 that drives the centrifugal pump 3 of FIG. 1 but also other storage units and a determination unit (with an executable program), etc., shown in FIG. 2, which are controlled by the CPU 31, and configurations thereof will be described later.

Figure 3:
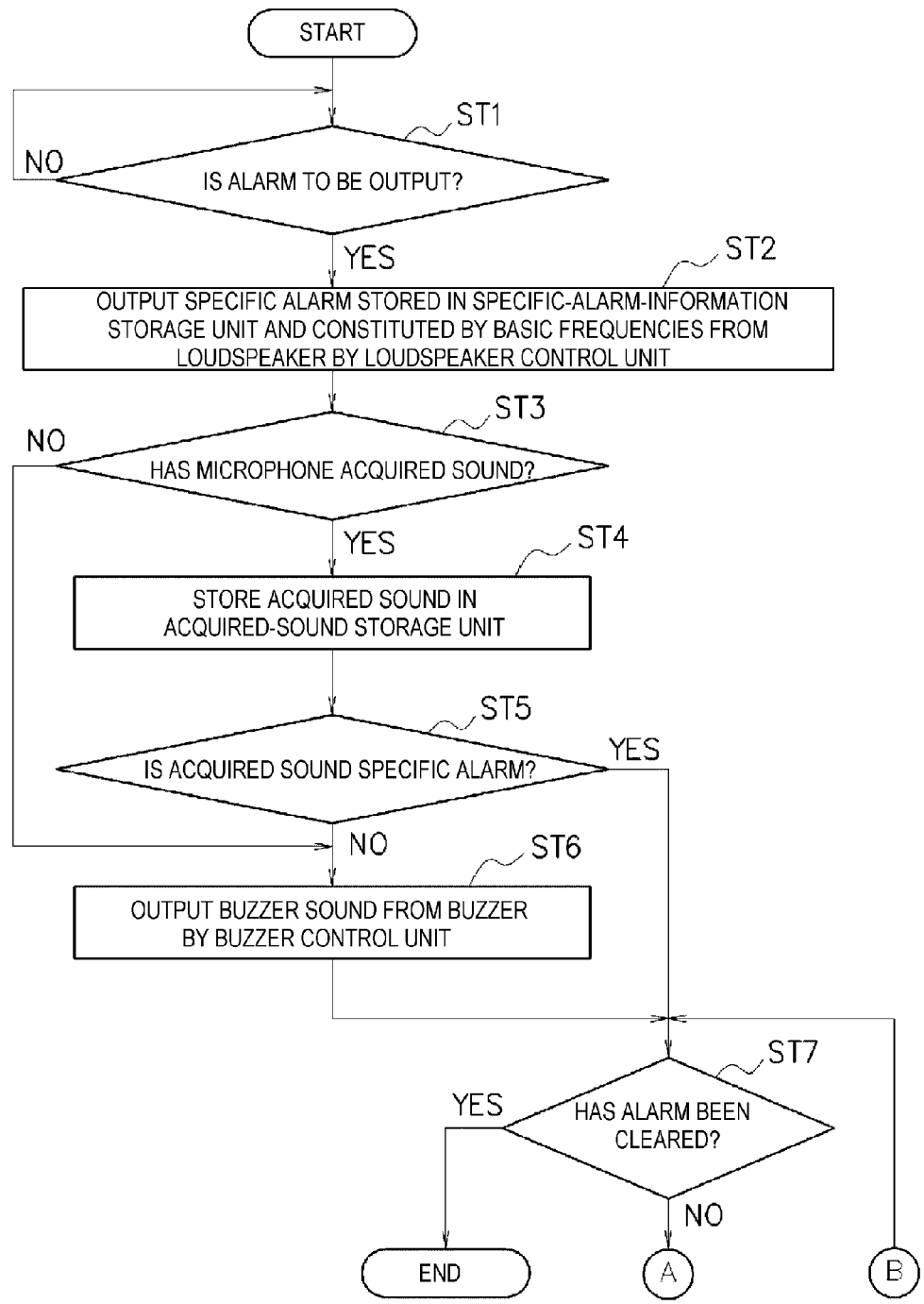
FIG. 3 is a schematic flowchart illustrating an example of main action, etc. of the extracorporeal circulator of FIG. 1.
Figure 4:
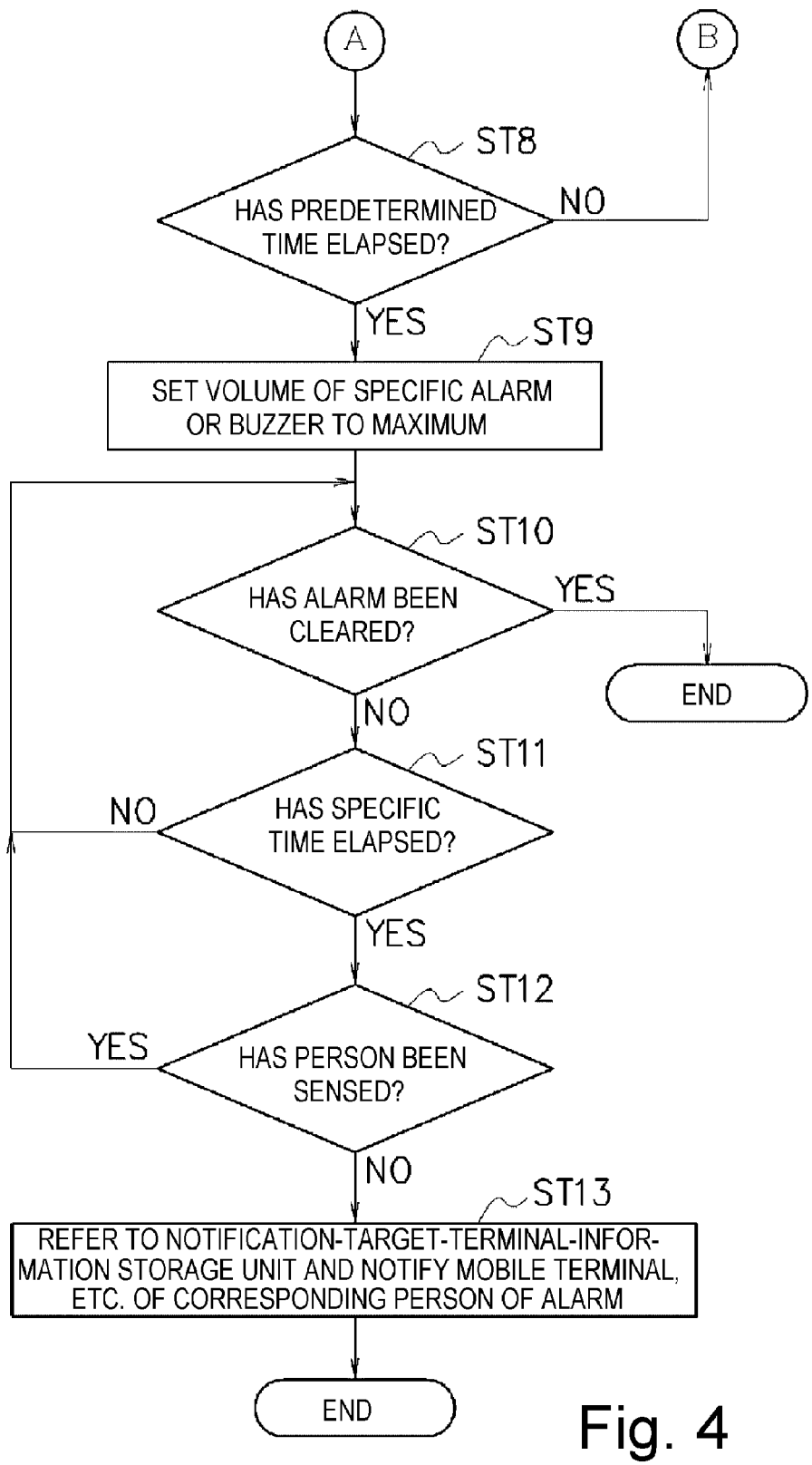
FIG. 4 is another schematic flowchart illustrating an example of the main action, etc. of the extracorporeal circulator of FIG. 1.

FIGS. 3 and 4 are schematic flowcharts illustrating an example of main actions, etc. of the extracorporeal circulator 1 of FIG. 1. Processing will now be described in accordance with these flowcharts, while configurations, etc. in FIGS. 1, 2, etc. will also be described. Furthermore, in the present embodiment, a case where a flow rate abnormality, a pressure abnormality, etc. occur to the extracorporeal circulator 1 installed for the patient P and an alarm signal (alarm) is output will be described by way of example.

First, in step ST (hereinafter, "ST") 1 of FIG. 3, the controller 10 determines whether to output an alarm signal (alarm) from detection values, etc. of the pressure sensor 15 and the blood flow rate sensor 14. As known in the art, specific alarm conditions can be correlated to specific detection values, and the alarm signal can have unique parameters that signal to a recipient which specific alarm condition has been detected. When the controller 10 determines that an alarm is to be output in ST1, the processing goes to ST2. In ST2, the loudspeaker control unit 36a, etc. refer to a "specific-alarm-information storage unit 41" of FIG. 2. This specific-alarm-information storage unit 41 stores therein information on a "specific alarm" composed of data on the basic frequencies of a sound to be output from the loudspeaker 36 (e.g., the tones of a musical scale do, re, mi, fa, so, etc., preferably composed of basic frequency components equal to or lower than 1 kHz). Owing to this, the loudspeaker control unit 36a, etc. control the loudspeaker 36 to output the "specific alarm" composed of the basic frequencies.

The processing then goes to ST3. In ST3, the controller 10 determines whether the microphone 38 has acquired an alarm sound from the loudspeaker 36. When the microphone 38 has acquired the alarm sound in ST3, the processing goes to ST4. In ST4, the alarm sound which has been acquired by the microphone 38 is stored in an "acquired-sound storage unit 42" of FIG. 2 (i.e., the sound detected by microphone 38 is digitally sampled and recorded).

The processing then goes to ST5. In ST5, the controller 10 determines whether the acquired sound is a match with the "specific alarm". Specifically, a "specific-alarm determination unit 43" (via an executable program) of FIG. 2 compares the sound which has been acquired by the microphone of the acquired-sound storage unit 42 with the "specific alarm" stored in the specific-alarm storage unit 41, and determines whether the acquired sound corresponds to the specific alarm. Namely, the specific-alarm-determination unit (program) 43 determines whether a frequency, etc. of the acquired sound match the basic frequency or sequence of frequencies, etc. of a basic alarm. In this way, the "specific-alarm determination unit (program) 43", etc. of FIG. 2 are an example of an output determination unit.

When it is determined that the acquired sound does not correspond to the specific alarm in ST5, a failure of the loudspeaker 36 is detected and the processing goes to ST6. In this way, in the present embodiment, it is determined whether the loudspeaker 36 has failed by the comparison with the "specific alarm" composed by the basic frequency; thus, it is possible to perform highly accurate determination.

In ST6, the buzzer 37 outputs a buzzer sound under the control, etc. of the buzzer control unit 37a of FIG. 2. In this way, in the present embodiment, when a failure, etc. occur to the loudspeaker 37, the buzzer sound is output, thereby making it possible to notify the nurse, etc. to be notified of the fact that an alarm condition has been detected and that the actions to generate a primary "specific alarm" were unsuccessful.

On the other hand, even when the microphone 38 could not acquire the sound, a failure of the loudspeaker 36 is determined and the processing goes to ST6, in which the buzzer 37 outputs the buzzer sound.

When the controller 10 determines that the sound which has been acquired by the microphone 38 is the specific alarm in ST5 or that the buzzer 37 has begun to output the buzzer sound in ST6 (i.e., the alarm is being output from the loudspeaker 36 or the buzzer 37 has buzzed), it is assumed that the nurse, etc., if hearing the alarm, will acknowledge by operating the input device 39 of FIG. 2 and will perform a corresponding operation for clearing the alarm condition. Owing to this, in ST7, it is determined whether the nurse, etc. have operated the input device 39 and executed the operation for clearing the alarm condition.

When the nurse, etc. have not executed the operation for clearing the alarm in ST7, the processing goes to ST8 in FIG. 4, in which it is determined whether a predetermined time has elapsed by referring to the timer 33 of FIG. 2. When it is determined that the predetermined time has elapsed in ST8, the processing goes to ST9. In ST9, it is assumed that the alarm has not gotten through to the nurse, etc. (the nurse, etc. does not hear the alarm), a volume of the loudspeaker 36 or the buzzer 37 is changed to, for example, maximum.

The processing goes to ST10. In ST10, it is determined again whether the nurse, etc. have operated the input device 39 and executed the operation for clearing the alarm. Namely, it is determined whether the alarm at this maximum volume enables the nurse, etc. to become aware of the fact of the alarm, and whether the nurse, etc. have operated the input device 39 and executed the operation for clearing the alarm. When the nurse, etc. have not executed the operation for clearing the alarm in ST10, the processing goes to ST11. In ST11, it is determined whether a second predetermined time has elapsed by referring to the timer 33 of FIG. 2.

When the second predetermined time has elapsed in ST11, the processing goes to ST12. In ST12, it is determined whether the motion sensor 35 has sensed the presence of a person in the vicinity of controller 10. When the motion sensor 35 has sensed the presence of a person in ST12, it is determined that the nurse, etc. are present around the extracorporeal circulator 1 and processes of ST10 and ST11 are repeated until the nurse, etc. operate the input device 39 and clear the alarm.

On the other hand, when it is determined that the motion sensor 35 has not sensed the presence of a nearby person in ST12, the processing goes to ST13. In ST13, it is assumed that the nurse, etc. are not present around the extracorporeal circulator 1 and a notification method other than output of the alarm from the loudspeaker 36, etc. is selected. Namely, the controller 10 first refers to a "notification-target-terminal-information storage unit 44" of FIG. 2. This notification-target-terminal-information storage unit 44 stores therein information of a communication address, etc. of the mobile terminal, etc. such as the cellular telephone 100 of the person such as the nurse, etc. to be notified of the alarm associated with the extracorporeal circulator 1. Owing to this, the controller 10 acquires the address, a telephone number, etc. of the cellular telephone 100 of the nurse, etc. to be notified of the alarm associated with the extracorporeal circulator 1 from the notification-target-terminal-information storage unit 44, and transmits the fact of the alarm to the cellular telephone 100.

In this way, in the present embodiment, it is possible to ensure that the nurse, etc. to be notified can be notified of the alarm associated with the extracorporeal circulator 1 and prevent the occurrence of serious matters to the patient P.

Figure 5:
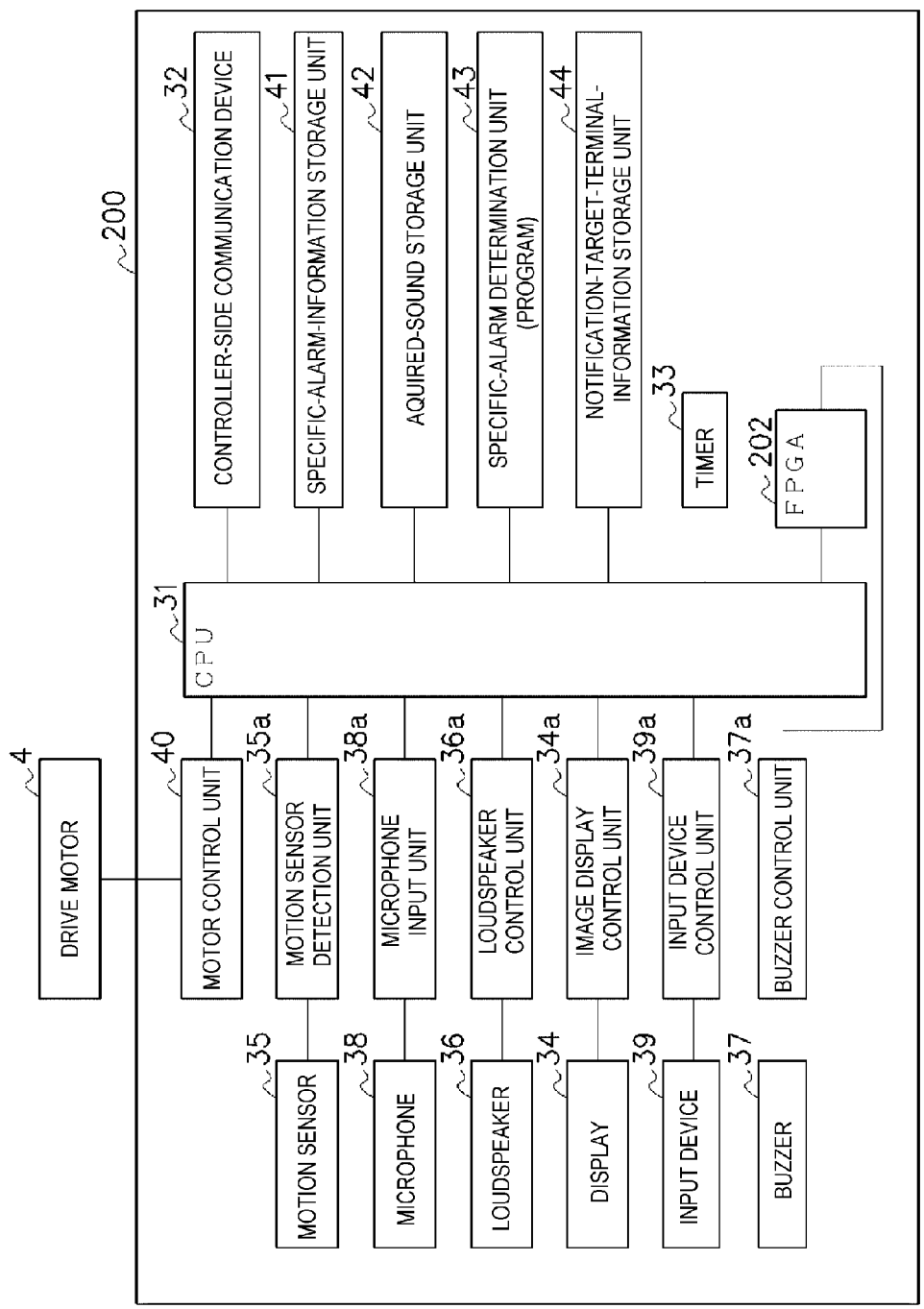
FIG. 5 is a schematic block diagram of a controller illustrating a modification of an embodiment of the present invention.

FIG. 5 is a schematic block diagram of a controller 200 for illustrating a modification of the embodiment of the present invention. Configurations of the present modification are similar to those of the abovementioned embodiment in many respects; therefore, common parts are denoted by the same reference symbols. etc. as those in the abovementioned embodiment and not described herein while differences are mainly described. The controller 200 in the present modification has an "FPGA 202" working together with the CPU 31, differently from the controller 10 in the abovementioned embodiment. This FPGA 202 is a Field-programmable gate array, which is an integrated circuit the configurations of which can be set by a purchaser or a designer after fabrication. The FPGA 202 enables cost reduction as compared with a case where a CPU is newly added. Furthermore, this FPGA 202 is configured to be able to control the buzzer 37 via the buzzer control unit 37*a*.

Moreover, in the present modification, the CPU 31 and the FPGA 202 are configured to monitor each other. Owing to this, when, for example, a failure occurs to the CPU 31 and the loudspeaker 36 is unable to output an alarm, the FPGA 202 promptly operates to enable the buzzer 37 to output an alarm. Owing to this, the controller 200 is configured to be able to further ensure the output of an alarm.

What is claimed is:

1. An alarm device for a medical instrument, comprising:
a controller for detecting a specific alarm condition;
a first alarm-signal sound output device selectably outputting a first audible alarm signal in response to the detection of the specific alarm condition;
an output determination unit including a microphone for determining whether the first alarm-signal sound output device is outputting the first audible alarm signal during the specific alarm condition;
a second audible alarm-signal output device selectably outputting a second audible alarm signal distinctive from the first audible alarm signal; and
an alarm-signal-output stop unit for manually clearing output of the first audible alarm signal and the second audible alarm signal;
wherein the controller is configured so that when the output determination unit determines that the first alarm-signal output device is not outputting the first audible alarm signal during the specific alarm condition, then the second alarm-signal output device outputs the second audible alarm signal, and
wherein the controller is configured so that when the stop unit does not manually clear the output of the audible alarm signals within a first predetermined time after the detection of the specific alarm condition, then an audible output characteristic of the audible alarm signals is changed.

2. The alarm device according to claim 1, further comprising:
a sensing unit to sense presence of a nearby person capable of recognizing the output of the audible alarm signals; and
a transmitter for communicating with a remote terminal device carried by a concerned person to be notified of the detection of the specific alarm condition;
wherein the controller is configured so that when the stop unit does not manually clear a selected alarm signal within a second predetermined time after change of audible output characteristic of the alarm signals and the sensing unit does not sense the presence of the nearby person, then the transmitter transmits information about occurrence of the specific alarm condition to the remote terminal device.

3. The alarm device according to claim 1, wherein the first audible alarm signal comprises a sequence of specific frequencies corresponding to the specific alarm condition that is detected.

4. An extracorporeal circulator comprising:
an artificial heart-lung apparatus; and
an extracorporeal circulation management device managing extracorporeal circulation of blood;
wherein the extracorporeal circulator includes an alarm device comprising:
a controller for detecting a specific alarm condition;
a first alarm-signal sound output device selectably outputting a first audible alarm signal in response to the detection of the specific alarm condition;
an output determination unit including a microphone for determining whether the first alarm-signal sound output device is outputting the first audible alarm signal during the specific alarm condition;
a second audible alarm-signal output device selectably outputting a second audible alarm signal distinctive from the first audible alarm signal; and
an alarm-signal-output stop unit for manually clearing output of the first audible alarm signal and the second audible alarm signal;
wherein the controller is configured so that when the output determination unit determines that the first alarm-signal output device is not outputting the first audible alarm signal during the specific alarm condition, then the second alarm-signal output device outputs the second audible alarm signal, and
wherein the controller is configured so that when the stop unit does not manually clear the output of the audible alarm signals within a first predetermined time after the detection of the specific alarm condition, then an audible output characteristic of the audible alarm signals is changed.

5. A control method for an alarm device of a medical instrument including a first alarm-signal output device selectably outputting a first audible alarm signal in response to detection of a specific alarm condition, an output determination unit including a microphone for determining whether the first alarm-signal output device is selectably outputting the first audible alarm signal, and an alarm-signal-output stop unit for manually clearing an output of the first audible alarm signal, the method comprising the steps of:

outputting, by a second alarm-signal sound output device, a second audible alarm signal distinctive from the first audible alarm signal when the output determination unit determines that the first alarm-signal sound output device is not outputting the first audible alarm signal during the specific alarm condition; and changing an audible output characteristic of the first audible alarm signal or the second audible alarm signal when the stop unit does not manually clear the output of the audible alarm signals within a predetermined time after detection of the specific alarm condition.

\* \* \* \* \*